United States Patent
Ma et al.

(10) Patent No.: US 12,421,527 B2
(45) Date of Patent: Sep. 23, 2025

(54) ARGONAUTE PROTEINS FROM PROKARYOTES AND APPLICATIONS THEREOF

(71) Applicant: Hubei University, Wuhan (CN)

(72) Inventors: Lixin Ma, Wuhan (CN); Yaping Wang, Wuhan (CN); Yang Liu, Wuhan (CN); Xiaoman Jiang, Wuhan (CN)

(73) Assignee: Hubei University, Wuhan (CN)

( * ) Notice: Subject to any disclaimer, the term of this patent is extended or adjusted under 35 U.S.C. 154(b) by 912 days.

(21) Appl. No.: 17/575,957

(22) Filed: Jan. 14, 2022

(65) Prior Publication Data

US 2022/0186254 A1 Jun. 16, 2022

Related U.S. Application Data

(63) Continuation of application No. PCT/CN2021/105421, filed on Jul. 9, 2021.

(30) Foreign Application Priority Data

Dec. 11, 2020 (CN) .......................... 202011457521.1

(51) Int. Cl.
*C12N 9/22* (2006.01)
*C12N 15/11* (2006.01)
*C12N 15/86* (2006.01)

(52) U.S. Cl.
CPC ............... *C12N 15/86* (2013.01); *C12N 9/22* (2013.01); *C12N 15/11* (2013.01); *C12N 2310/14* (2013.01); *C12N 2740/10043* (2013.01); *C12N 2740/15043* (2013.01); *C12N 2800/80* (2013.01)

(58) Field of Classification Search
CPC .............................. C12N 9/22; C12N 2310/14
See application file for complete search history.

(56) References Cited

PUBLICATIONS

O'Green, Unexpected binding behaviors of bacterial Argonautes in human cells cast doubts on their use as targetable gene regulators. PLoS One13(3): e0193818 (Year: 2018).*
Javidi-Parsijani, No evidence of genome editing activity from Natronobacterium gregoryi Argonaute (NgAgo) in human cells. PLoS One 12 (5): e0177444 (Year: 2017).*
Wu, NgAgo-gDNA system efficiently suppresses hepatitis B virus replication through accelerating decay of pregenomic RNA. Antiviral Research 145: 20e23 (Year: 2017).*

* cited by examiner

*Primary Examiner* — J. E. Angell
*Assistant Examiner* — Julio Washington Gomez Rodriguez
(74) *Attorney, Agent, or Firm* — WPAT, PC

(57) ABSTRACT

Argonaute proteins from prokaryotes (pAgos) and applications thereof are provided, the pAgo is from a mesophilic prokaryote of *Kurthia massiliensis* and named as KmAgo, the pAgos and applications thereof are capable of site-specific modification of intracellular and extracellular genetic material, and thus can be effectively applied to many fields of biotechnology, such as nucleic acid detection, gene editing and gene modification, and provide a new tool for gene editing, modification and molecular detection of the pAgo polypeptides.

6 Claims, 5 Drawing Sheets
Specification includes a Sequence Listing.

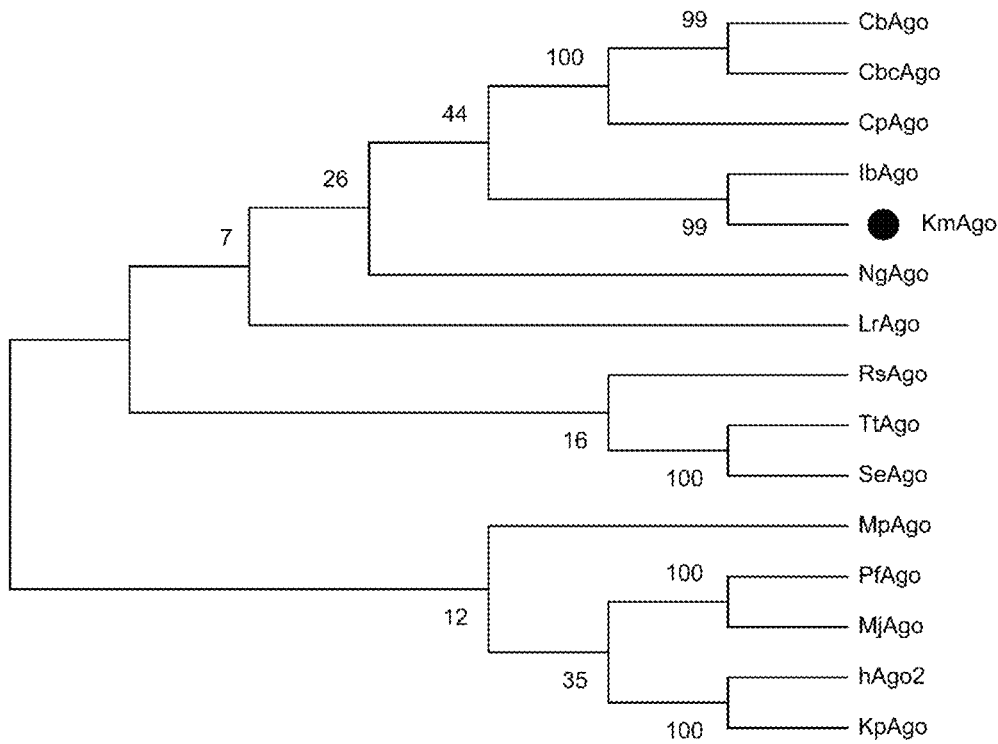

FIG. 1

| Protein | Source | D | E | D | X | Identity(%) |
|---|---|---|---|---|---|---|
| TtAgo | -Thermus thermophilus | AVGFDAGGR | AQAGERIPQ | LLLRDGRVP | LHLADRLVK | 17.95 |
| CbAgo | -Clostridium butyricum | FIGLDVGTR | PQSGEKIAE | VIHRDGFSR | TGYADKICK | 22.26 |
| NgAgo | -Natronobacterium gregoryi | FIGIDVSRS | PQLGEKLQS | VIHRDGFMN | TAYADQAST | 21.34 |
| RsAgo | -Rhodobacter Sphaeroides | VVGMGLAEL | ECEYEGYSD | RVVFHAHRP | IFYSERIAE | 14.06 |
| MpAgo | -Marinitoga piezophila | YIGIDLSHD | LELNEKMNL | FILRDGRFI | LRIANKVAL | 18.34 |
| LrAgo | -Limnothrix rosea | IVGLDVSPR | VIDGEILPE | LIHRDGLFP | TYYADKIST | 21.09 |
| IbAgo | -Intestinibacter bartlettii | YIGLDVCRE | HQSGEKIQI | VFHPDGINR | TYYADLSSI | 29.67 |
| CbcAgo | -Clostridium. butyricum CWBI1009 | FIGLDVGTR | PQSGERIAE | VIHPDGFSR | TGYADKICK | 22.26 |
| CpAgo | -Clostridium perfringens | FVGLDVGTR | PQNGEKINT | VIHRDGFSR | TGYADKICK | 22.21 |
| SeAgo | -Synechococcus elongates | IIGFDTGTN | VQRGETFSG | LLMRDGLVQ | LHLADRSSK | 18.70 |
| PfAgo | -Pyrococcus furiosus | IIGIDVAPM | EQRGESVDM | LLLRDGRIT | VRYAEKFAN | 18.30 |
| MjAgo | -Methanocaldococcus jannaschii | IMGLDTGLG | PAPGERLHL | LFLRDGPIQ | IRYADKFVK | 15.77 |
| hAgo2 | -Homo sapiens | FLGADVTHP | QHRQEIIQD | IFYPDGVSE | AYYAHLVAF | 14.97 |
| KpAgo | -Kluyveromyces Polysporus | VLGSDVTHY | DGPGEIIT | MYFRDGVSV | VYYADLLCT | 13.55 |
| KmAgo | -Kurthia massiliensis | FIGIDVSHE | ILAGEKIDD | TIHRDGFWR | IRYADLSAT | 100.00 |
| KmAgo_DM | -Kurthia massiliensis double mutant | FIGIAVSHE | ILAGEKIDD | TIHRAGFWR | IRYADLSAT | |

FIG. 2

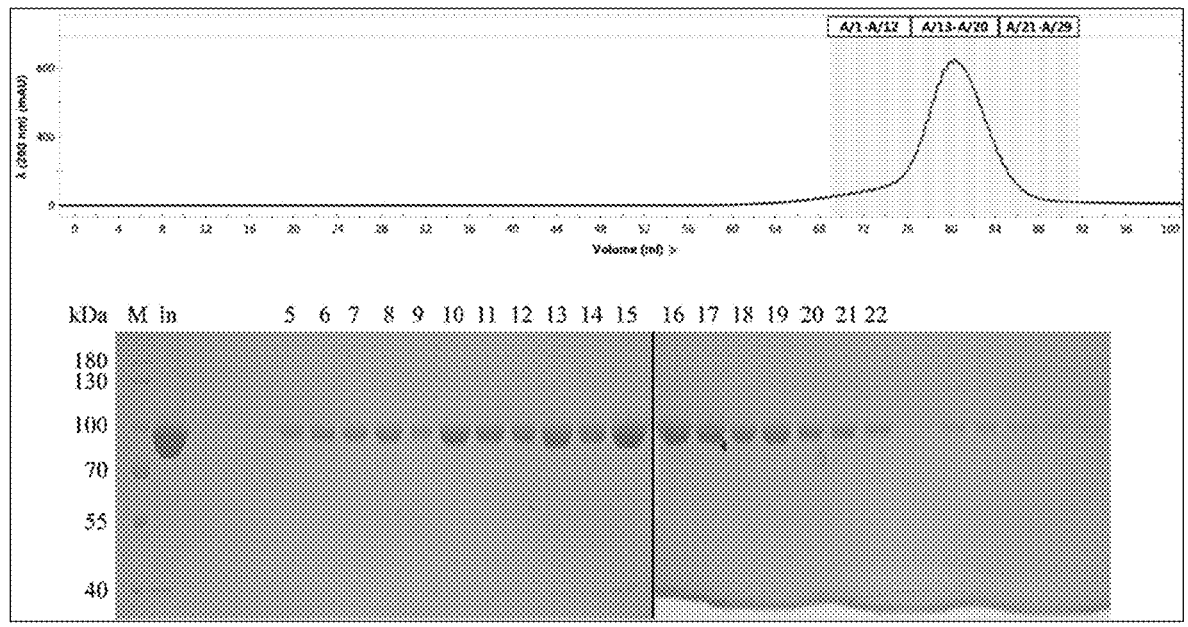
FIG. 3
```
gDNA   5' TGAGGTAGTAGGTTGTAT  SEQ ID NO: 3
          |||||||||||||||||
tDNA   3' TGCTCCATCATCCAACATATCATTCGAACCGTGACCGGCAGCAAA  SEQ ID NO: 4
gRNA   5' UGAGGUAGUAGGUUGUAU  SEQ ID NO: 5
          |||||||||||||||||
tRNA   3' UGCUCCAUCAUCCAACAUAUCAUUCGAACCGUGACCGGCAGCAAA  SEQ ID NO: 6
```
FIG. 4
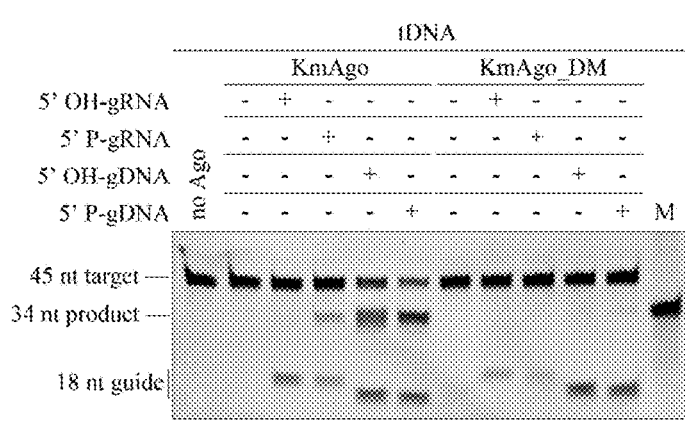
FIG. 5

SEQUENCE LISTING

```
<160> NUMBER OF SEQ ID NOS: 6

<210> SEQ ID NO 1
<211> LENGTH: 721
<212> TYPE: PRT
<213> ORGANISM: Artificial Sequence
<220> FEATURE:
<223> OTHER INFORMATION: KmAgo amino acid sequence

<400> SEQUENCE: 1

Met Glu Ala Tyr Ile Thr Glu Met Val Ser Arg Glu Arg Ala Asn Glu
1               5                   10                  15

Leu Glu Val Tyr Val Tyr Val Phe Pro Arg Lys Gln Ser Asp Asn Asn
            20                  25                  30

Tyr Glu Gly Val Tyr His Ile Met Arg Ala Trp Gln Arg Ala Asn Asp
        35                  40                  45

Leu Pro Leu Ala Tyr Asn Gln His Thr Ile Met Ala Phe Ser Pro Val
    50                  55                  60

Arg His Met Cys Gly Tyr Thr Pro Met Glu Thr Gln Lys Arg His Ile
65                  70                  75                  80

Asn Ile Asp Ser Pro Phe Glu Arg Ala Leu Leu Glu Arg Leu Ile Lys
                85                  90                  95

Asn Ser Leu Ile Phe Thr Ala Glu Arg His Leu His Ala Lys Arg Val
            100                 105                 110

Gly His Ala Leu Arg Leu Asn Gln Val Gln Gln Ile Arg Gln Val Ile
        115                 120                 125

Ile Tyr Glu Ala Ile Glu Leu Tyr Val Asn Ile Ile Glu Asn Arg Ile
    130                 135                 140

Ser Ile Gly Phe His Leu Thr His Gln Phe Glu Tyr Val Tyr Thr Leu
145                 150                 155                 160

Gln Ser Met Ile Glu Gln Gly Lys Thr Ile Arg Pro Gly Met Arg Val
                165                 170                 175

Val His Ser Asn Gly Arg Gln His Tyr Thr Tyr Thr Val Glu Asn Val
            180                 185                 190

Ala Thr Tyr Gly Val Thr Asp Arg Cys Pro Leu Leu Gln Thr Ser Ile
        195                 200                 205

Tyr Gln Tyr Tyr Val Glu Lys Gly Ala Gln His Ile Leu Arg Thr Phe
    210                 215                 220

Thr Arg Ser Thr Arg Val Ile His Val Arg Thr Lys Glu Gln Arg Leu
225                 230                 235                 240

Ser Tyr Ala Ala Thr Leu Leu Lys Pro Leu Cys Thr Phe Glu Thr Met
                245                 250                 255

Gln Pro Gln Asp Val Leu Asn Val Ser Lys Cys Ile Lys Leu Ser Ala
            260                 265                 270

Ser Lys Arg Met Lys Cys Thr Tyr Arg Trp Ile Gln Gln Leu Arg Ala
        275                 280                 285

Gln Tyr Arg His Leu Thr Phe Ala Pro Asn Pro Phe Thr Ile Ala Gln
    290                 295                 300
```

```
Asn Gly Tyr Lys Leu Asp Gln Leu Ser Thr Pro Lys Val His Phe His
305                 310                 315                 320

Arg Asp Tyr Ala Thr Val Val Ser Gly Met Lys Thr Gly Lys Leu Tyr
                325                 330                 335

Lys Gly Gly Asn Ile Lys Ile Ser Val Leu Phe Asp Glu Asp Phe Tyr
                340                 345                 350

Leu Lys His His Ile Thr Lys Lys Asp Ile Tyr Gln Phe Ile Ala Val
                355                 360                 365

Leu Gln Lys Ile Ala Ile Ala Gln Gly Val Asn Met Thr Ile Ser Thr
    370                 375                 380

Ser Thr Lys Ser Ile Thr Gly Lys Phe Thr Asp Asp Phe Phe His His
385                 390                 395                 400

Phe Thr Glu Glu Val Glu Ala Leu Gln Pro Ile Phe Ala Gln Thr Thr
                405                 410                 415

Val Leu Ala Phe Ile Thr Ser Thr His Leu Ser Asn Lys Lys Thr Arg
                420                 425                 430

Ser Tyr Gln Leu Leu Lys Gln Tyr Phe Gly Gly Lys Trp Asp Ile Ala
                435                 440                 445

Ser Gln Val Ile Thr Glu Lys Thr Ile Glu Ala Phe Gln Lys Ile Leu
450                 455                 460

His Lys His Gly Leu Lys Asn Phe Tyr Pro Asn Asp Glu Gln His Cys
465                 470                 475                 480

Leu Arg Val Ile Asp Val Leu Lys Asn Glu Ser Phe Tyr Tyr Thr Val
                485                 490                 495

Met Asn Ile Leu Leu Gly Val Tyr Val Lys Ser Gly Ile Gln Pro Trp
                500                 505                 510

Ile Leu Ala Asn Thr Thr His Ser Asp Cys Phe Ile Gly Ile Asp Val
                515                 520                 525

Ser His Glu Asn Gly Asn Ser Ala Ala Gly Met Met Asn Val Ile Gly
    530                 535                 540

Ser Gln Gly His Leu Ile Gln Gln Ala Pro Leu Asn Gly Ile Leu Ala
545                 550                 555                 560

Gly Glu Lys Ile Asp Asp Thr Leu Leu Ala Asn Leu Leu Lys Gln Met
                565                 570                 575

Ile Lys Ala Tyr His Thr Gln Phe Gln Arg Phe Pro Lys His Ile Thr
                580                 585                 590

Ile His Arg Asp Gly Phe Trp Arg Glu His Thr Ala Leu Val Glu Lys
    595                 600                 605

Lys Pro Asn Arg Arg Met Ala Phe Phe Asn Ser Val Asp Asn Thr Phe
610                 615                 620

Ser Thr Arg Gln Gly Thr Val Tyr Gln Arg Gly Asn Glu Ala Phe Leu
625                 630                 635                 640

Cys Ala Thr Asn Pro Gln Gln Lys Val Gly Met Ala Gln Pro Ile Lys
                645                 650                 655

Ile His Gln Val Thr Lys Thr Leu Pro Phe Ser His Ile Ile Glu Asp
                660                 665                 670

Val Tyr Asn Leu Ser Phe Leu His Ile His Ala Met Asn Lys Met Arg
                675                 680                 685

Leu Pro Ala Thr Ile His Tyr Ala Asp Leu Ser Ala Thr Ala Tyr Gln
                690                 695                 700

Arg Gly Gln Val Met Pro Arg Ser Gly Asn Gln Thr Asn Leu Pro Phe
705                 710                 715                 720

Val
```

<210> SEQ ID NO 2
<211> LENGTH: 2214
<212> TYPE: DNA
<213> ORGANISM: Artificial Sequence
<220> FEATURE:
<223> OTHER INFORMATION: KmAgo polynucleotide sequence

<400> SEQUENCE: 2

| | | | | | |
|---|---|---|---|---|---|
| atggaagctt | acatcaccga | gatggtgtcc | agagaaagag | ctaacgagtt | ggaggtttac | 60 |
| gtctacgtgt | tcccaagaaa | gcagtccgac | aacaactacg | agggtgtcta | ccacattatg | 120 |
| agagcttggc | aaagagccaa | cgacttgcca | ttggcttaca | accagcacac | catcatggct | 180 |
| ttctcaccag | ttagacacat | gtgcggttac | accccaatgg | aaactcagaa | gagacacatc | 240 |
| aacatcgact | ccccattcga | gagctttg | ttggagagac | tgatcaagaa | ctccttgatc | 300 |
| ttcactgccg | agagacactt | gcatgctaag | agagttggtc | acgccttgag | attgaaccag | 360 |
| gttcagcaaa | tcaggcaggt | catcatctac | gaggctatcg | agttgtacgt | caacatcatc | 420 |
| gagaacagga | tctccatcgg | tttccacttg | actcaccaat | tcgagtacgt | ctacaccctg | 480 |
| cagtccatga | ttgagcaggg | taagactatc | agaccaggta | tgagagttgt | ccactccaac | 540 |
| ggtagacagc | actacactta | caccgttgag | aacgttgcta | cctacggtgt | tactgacaga | 600 |
| tgtcctttgt | tgcagacctc | catctaccag | tactacgttg | agaagggtgc | tcagcacatc | 660 |
| ttgagaactt | tcaccagatc | caccagagtc | atccacgtta | ggaccaaaga | gcagagattg | 720 |
| tcctacgctg | ctaccttgtt | gaagccattg | tgtaccttcg | agactatgca | gccacaggac | 780 |
| gttttgaacg | tttccaagtg | catcaagttg | tccgcctcca | agagaatgaa | gtgcacctac | 840 |
| agatggattc | agcagttgag | agcccagtac | agacacttga | ctttcgcccc | aaatccattc | 900 |
| actatcgccc | agaacggtta | caagttggac | cagttgtcta | ccccaaaggt | ccacttccat | 960 |
| agagactacg | ctactgttgt | ctccggtatg | aagaccggta | agttgtacaa | aggtggtaac | 1020 |
| atcaagatct | ccgtcctgtt | cgatgaggac | ttctacttga | agcaccacat | caccaagaag | 1080 |
| gatatctacc | aattcattgc | cgtcctgcag | aagatcgcta | ttgctcaggg | tgttaacatg | 1140 |
| accatctcca | cctccactaa | gtccatcact | ggtaagttca | ccgacgattt | cttccaccac | 1200 |
| ttcaccgaag | aggttgaagc | cttgcaacct | atcttcgctc | agactactgt | tctggccttc | 1260 |
| atcacttcta | cccacctgtc | caacaagaaa | ccaggtcct | accaattgct | gaagcagtac | 1320 |
| tttggtggta | agtgggacat | tgcttcccag | gttatcaccg | aaaagactat | cgaggccttc | 1380 |
| caaaagatcc | tgcacaagca | cggtctgaag | aactttacc | caaacgacga | gcagcactgc | 1440 |
| ttgagagtta | ttgacgtctt | gaagaacgag | tccttctact | acaccgtcat | gaacatcctg | 1500 |
| ctgggtgttt | acgttaagtc | cggtattcag | ccatggatct | tggctaacac | tactcactcc | 1560 |
| gactgcttca | tcggtattga | cgtttctcac | gagaacggta | actctgctgc | tggtatgatg | 1620 |
| aacgttattg | gttcccaggg | tcacttgatc | caacaggctc | cattgaacgg | tattttggcc | 1680 |
| ggtgaaaaga | tcgacgacac | cttgttggcc | aatctgttga | agcagatgat | caaggcctac | 1740 |
| cacactcagt | tccagagatt | cccaaagcac | atcactatcc | accgtgacgg | ttttggaga | 1800 |
| gaacacactg | ctttggtcga | gaagatcatg | tctcactacg | agatcaccta | cgacatcgtc | 1860 |
| gagatcatca | aaaagccaaa | cagaaggatg | gccttcttca | actccgttga | caacactttc | 1920 |
| tccaccagac | agggtactgt | ttaccagaga | ggtaacgagg | cttttcctgtg | tgctacaaac | 1980 |
| ccacagcaaa | aggttggtat | ggctcagcca | atcaagattc | accaggttac | caagaccttg | 2040 |

```
ccattctctc acattatcga ggacgtgtac aacctgtcct tcttgcacat tcacgccatg    2100
aacaagatga gattgccagc cactattcac tacgctgact tgtctgctac tgcttaccaa    2160
cgtggtcagg ttatgcctag atctggtaac cagaccaacc tgccattcgt ttaa          2214

<210> SEQ ID NO 3
<211> LENGTH: 18
<212> TYPE: DNA
<213> ORGANISM: Artificial Sequence
<220> FEATURE:
<223> OTHER INFORMATION: KmAgo guide DNA sequence

<400> SEQUENCE: 3
tgaggtagta ggttgtat                                                  18

<210> SEQ ID NO 4
<211> LENGTH: 45
<212> TYPE: DNA
<213> ORGANISM: Artificial Sequence
<220> FEATURE:
<223> OTHER INFORMATION: KmAgo target DNA sequence

<400> SEQUENCE: 4
tgctccatca tccaacatat cattcgaacc gtgaccggca gcaaa                    45

<210> SEQ ID NO 5
<211> LENGTH: 18
<212> TYPE: RNA
<213> ORGANISM: Artificial Sequence
<220> FEATURE:
<223> OTHER INFORMATION: KmAgo guide RNA sequence

<400> SEQUENCE: 5
ugagguagua gguuguau                                                  18

<210> SEQ ID NO 6
<211> LENGTH: 45
<212> TYPE: RNA
<213> ORGANISM: Artificial Sequence
<220> FEATURE:
<223> OTHER INFORMATION: KmAgo target RNA sequence

<400> SEQUENCE: 6
ugcuccauca uccaacauau cauucgaacc gugaccggca gcaaa                    45
```

ARGONAUTE PROTEINS FROM PROKARYOTES AND APPLICATIONS THEREOF

TECHNICAL FIELD

The disclosure relates to the technical field of molecular biology, and more particularly to Argonaute proteins from prokaryotes and applications thereof.

SEQUENCE LISTING

This application incorporates by reference the material in the sequence listing submitted via ASCII text file titled 21013JHG-USP1-sl-R.txt, with the date of creation being Jul. 3, 2025, and the size of the ASCII text file being 9,762 bytes. No new matter is entered.

BACKGROUND

Currently, eukaryotic Argonaute proteins (shorted as eAgos, also referred to as Argonaute proteins from eukaryotes) are capable of catalyzing Ribonucleic Acid (shorted as RNA) cleavage reactions guided by RNA guides (shorted as gRNAs) under room temperature conditions, and play a key role in the RNA interference (shorted as RNAi) pathway in vivo. Prokaryotic Argonaute proteins (shorted as pAgos, also referred to as Argonaute proteins from prokaryotes) are more diverse in function and structure than the eAgos, but their physiological functions have long been elusive. Early studies focused on pAgos of thermophilic organisms, except for Argonaute proteins from *Marinitoga piezophila* (shorted as MpAgo) which favor the use of 5'-terminal hydroxylated (5'OH) DNA guide (shorted as gDNA) to cleave target single-stranded deoxyribonucleic acids (shorted as ssDNAs) and target RNAs, the other pAgos from thermophilic organisms favor the use of 5'-terminal phosphorylated (5'P) gDNA to cleave target ssDNAs and target RNAs. The pAgos from thermophilic organisms have low levels of cleavage activities of gDNA guided target ssDNAs and/or target RNAs under mesophilic conditions, which limits the application and development of pAgos-based RNA editing technologies. Recent studies have begun to focus on pAgos from mesophilic organisms, aiming at the finding of pAgos that can efficiently cleave target DNAs and/or target RNAs under mesophilic conditions. Almost all of the characterized mesophilic pAgos prefer to catalyze gDNA-guided target DNA cleavage at mesophilic temperatures while having low RNA cleavage activities. An Argonaute protein from *Natronobacterium gregory* (shorted as NgAgo) can cleave a target RNA guided by gDNA at room temperature, but its cleavage site is uncertain, and it has not been shown to cleave highly-structured RNA. In addition, although eAgos are thought to have evolved from pAgos, currently characterized pAgos do not catalyze gRNA-guided target RNA cleavage reactions at mesophilic temperatures like the eAgos.

There has long been widespread interest in programmable endonucleases of target RNAs, as such endonucleases can be applied to RNA structure-function studies, nucleic acid detection fields, RNA nanotechnology, and RNA therapeutics. The early methods used have certain limitations, such as the need for extensive redesign or additional selective evolution for each target. The newly developed clustered regularly interspaced short palindromic repeat (CRISPR)/CRISPR-associated (Cas) nucleases are rapidly being applied in the fields of nucleic acid detection and viral clearance. However, CRISPR/Cas nucleases require the gRNA which must be transcribed and purified in vitro or purchased in a large quantity. In addition, CRISPR/Cas nucleases have not yet shown the ability to recognize structured RNA elements. Some eAgos are capable of cleaving almost all types of RNAs at mesophilic temperatures under the guide of gDNA, but RNAi pathways exist in most plant and animal cells, so that these eAgos may interfere with the cell's own RNAi function, which hinders the application of eAgos to intracellular RNA editing. There is no RNAi pathway in prokaryotic organisms, so pAgos may not affect the RNAi function of the cells themselves.

There is still an urgent need in the field of RNA editing for pAgos that can function under room temperature and be applied to RNA editing in plant and animal cells.

Through the above analysis, the problems and defects of the prior art are that: RNA editing refers to a process of altering genetic information at the mRNA level. RNA editing is related to biological cell development and differentiation, and is an important way of gene expression regulation. The prior art does not have pAgos that can effectively target cleave various types of RNAs under room temperature and be applied to RNA editing in plant and animal cells. General RNAi technology requires the use of double-stranded RNA (shorted as dsRNA), chemical synthesis of the dsRNA is expensive and has a long customization cycle, in vitro transcription of the dsRNA is relatively inexpensive but difficult and time-consuming to operate, and a gene interference effect of short hairpin RNA (shRNA) expression plasmid is durable and economical but time-consuming to prepare and there is non-specific gene suppression, etc. The CRISPR-based technology also requires the use of long gRNA, which has the same problems as RNAi technology, and in addition, Cas proteins (e.g. Cas13a) relies on a specific motif near the target site to recognize and bind the target, which limits the scope of what can be edited. Recently, Cas proteins have also been found to have very strong non-specific "collateral" activity, which raises concerns about their possible off-target responses.

The significance of addressing the above problems and defects is that it is generally believed pAgos may not interfere with the RNAi pathway in plant and animal cells, the DNA guides (gDNAs) are shorter in synthesis cycle and cheaper than RNA, and pAgos do not depend on specific motifs near the target sites to recognize and bind the target RNAs, which makes it possible to edit arbitrary sites of RNA. In addition, the protein size of pAgos is approximately three-fourths that of each of eAgos and one-half that of Cas proteins, which may be easier to transfect into cells. In conclusion, pAgos, which can specifically cleave various types of RNAs, are a novel and effective tool for RNA editing and will greatly contribute to the development of the RNA editing field.

SUMMARY

In order to overcome the shortcomings of the prior art, the disclosure provides pAgos and applications thereof.

Specifically, an Argonaute protein from prokaryote (pAgo), the pAgo is from a mesophilic prokaryote of *Kurthia massiliensis* and named as KmAgo; and the pAgo is consisted of an amino acid sequence as shown in SEQ ID NO: 1 or an amino acid sequence with at least 50% identity to the amino acid sequence as shown in SEQ ID NO: 1.

In an embodiment, the pAgo has at least 80%, preferably at least 90%, more preferably at least 95% identity to the amino acid sequence as shown in SEQ ID NO: 1.

In an embodiment, the pAgo has a nuclease activity at 10 Celsius degrees (° C.) to 80° C., and preferably at 32 to 44° C.

In an embodiment, the pAgo has the nuclease activity preferably at 37° C.

Another object of the disclosure is to provide a pAgo complex formed by the pAgo, a length of an ssDNA guide of the pAgo complex is 9 to 50 numbers of nucleotides, preferably 12 to 30 numbers of nucleotides, and more preferably 15 to 20 numbers of nucleotides, such as 16, 18 or 20 numbers of nucleotides.

In an embodiment, a length of an RNA guide of the pAgo complex is 10 to 30 numbers of nucleotides, preferably 12 to 25 numbers of nucleotides, and more preferably 12 to 18 numbers of nucleotides, such as 13, 15 or 18 numbers of nucleotides.

In an embodiment, target RNAs of the respective pAgo and pAgo complex each are no highly-structured, or are highly-structured.

In an embodiment, the target RNAs of the respective pAgo and pAgo complex each are the double-stranded RNA (dsRNA).

In an embodiment, the target RNAs of the respective pAgo and pAgo complex each are an in vitro transcribed RNA.

In an embodiment, the target RNAs of the respective pAgo and pAgo complex each are a viral genomic RNA.

In an embodiment, the target RNAs of the respective pAgo and pAgo complex each are one of a messenger RNAs (i.e., mRNA) and other intracellular RNAs.

In an embodiment, guides of the respective pAgo and pAgo complex each are a 5'-terminal phosphorylated ssDNA.

In an embodiment, the guides of the respective pAgo and pAgo complex each are a 5'-terminal hydroxylated ssDNA.

In an embodiment, the guides of the respective pAgo and pAgo complex each are a 5'-terminal phosphorylated RNA.

In an embodiment, nuclease activities of the respective pAgo and pAgo complex require the presence of at least one cation selected from the group consisting of manganese ion ($Mn^{2+}$), magnesium ion ($Mg^{2+}$), calcium ion ($Ca^{2+}$), copper ion ($Cu^{2+}$), iron ion ($Fe^{2+}$), cobalt ion ($Co^{2+}$), zinc ion ($Zn^{2+}$) and nickel ion ($Ni^{2+}$) and any combinations thereof.

In an embodiment, at least one cation of the respective pAgo and pAgo complex is $Mn^{2+}$.

In an embodiment, the pAgo and a pAgo of the pAgo complex both are extracted or synthesized.

In an embodiment, a target DNA of the pAgo is the ssDNA.

In an embodiment, the target DNA of the pAgo is the dsDNA.

Another object of the disclosure is to provide a polynucleotide encoding the described above pAgo.

Another object of the disclosure is to provide a method of in vitro cleaving RNA based on the pAgo, the method includes:
  step 1, forming a pAgo-guide complex based on the pAgo and an ssDNA guide;
  step 2, making the pAgo-guide complex be in contact with a target RNA, the target RNA has a nucleotide sequence complementary to more than half of a sequence of the ssDNA guide, and the pAgo-guide complex cleaves the target RNA at a specific site.

Another object of the disclosure is to provide a method of intracellular cleaving target RNA based on the pAgo; the method includes:

(1) mixing the pAgo with an ssDNA guide to form a pAgo-guide complex according to the pAgo and the ssDNA guide;
(2) transferring the pAgo-guide complex into a cell by transformation, transfection or transduction; a sequence of the pAgo-guide complex is complementary paired with more than half of a sequence of a RNA in the cell.

In an embodiment, the method of intracellular cleaving target RNA occurs in a cell in situ of a living tissue, an organ, or an animal including human.

Another object of the disclosure is to provide a method for the site-specifically modifying genetic material of cell based on the pAgo, the method for the site-specifically modifying genetic material of cell includes:

Introducing an expression vector containing a polynucleotide sequence of the pAgo into a cell, introducing one or more ssDNA guides simultaneously or not simultaneously with the introducing the expression vector containing the polynucleotide sequence of the pAgo into the cell, and expressing the pAgo in the cell.

In an embodiment, the method for the site-specifically modifying genetic material of cell occurs in an isolated cell.

In an embodiment, the method for the site-specifically modifying genetic material of cell occurs in a cell in situ of a living tissue, an organ or an animal including a human.

In an embodiment, the pAgos are encoded by one expression vector.

In an embodiment, the expression vector containing the polynucleotide sequence of the pAgo is contained in a viral vector.

In an embodiment, the cell is a prokaryotic cell.

In an embodiment, the cell is a eukaryotic cell.

Another object of the disclosure is to provide a viral vector including the described above expression vector.

In an embodiment, the viral vector is a lentiviral vector or a retroviral vector.

Another object of the disclosure is to provide a kit including the described above pAgo and the ssDNA guide.

In combination with all the embodiments described above, the disclosure has the advantage and positive effect that: the disclosure relates to pAgo polypeptides capable of cleaving target nucleotide sequences under the guidance of the nucleic acid chain. The disclosure further provides the expression vector including nucleic acids encoding the polypeptides, the complexes, the kit and the methods for cleaving and editing target nucleic acids in a sequence-specific manner. The polypeptides, nucleic acids, expression vectors, complexes, kits and methods of the disclosure are capable of site-specific modification of intracellular and extracellular genetic material and thus can be effectively applied in many fields of biotechnology, such as nucleic acid detection, gene editing and gene modification, and provide a new tool for gene editing, modification and molecular detection of the pAgo polypeptides.

The protein of the disclosure has binding activity to the single-stranded DNA (ssDNA) guide or the RNA guide and has nuclease activity to the target RNA and/or the DNA, such that site-specific cleavage of the target RNA and/or the DNA occurs when the ssDNA guide and/or the RNA guide that have the sequence paired with more than half of the sequence of the target RNA and/or the DNA bind to the pAgo to form the pAgo-guide complex and the pAgo-guide complex is conjugated to the target RNA and/or the DNA.

The disclosure is capable of cleaving target DNA and/or RNA when forming complexes with single-stranded DNA (ssDNA) guides and/or RNA guides, site-specificity can be modulated by selecting DNA guides and/or RNA guides with specific nucleotide sequences. The disclosure further relates to the use of the pAgo-guide complex for site-specific modification of genetic material, which may be extracted from or within a cell. Thus, the disclosure relates to the pAgo used in RNA editing technology.

The pAgo of the disclosure is capable of specifically cleaving highly-structured RNA by using a DNA guide with the length of 18 nucleotides (nt), which makes it possible to cleave various types of RNAs. Moreover, the DNA guide has a short synthesis cycle time and low price compared to RNA, which can greatly save costs. In addition, the pAgo of the disclosure does not have to rely on specific motifs near the targeting site to recognize and bind the target, and the DNA guide is designed conveniently without considering site restriction. The pAgo of the disclosure has strong cleavage activity, which strictly depends on the complementary pairing of the guide and the target, without the non-specific "collateral" activity of Cas proteins, and has better specificity. Further, mutation of the active site of the pAgo can obtain the pAgo with complete loss of cleavage activity, which can be fused with other effector proteins, further expanding its application. It is generally believed that the pAgos cannot interfere with the RNAi pathway in plant and animal cells, which makes RNA editing by using the techniques of the disclosure likely to have minimal impact on the endogenous pathway in plant and animal cells.

BRIEF DESCRIPTION OF DRAWINGS

In order to more clearly illustrate the technical solutions of the embodiments of the disclosure, the following is a brief description of the accompanying drawings to be used in the embodiments of the disclosure. Obviously, the accompanying drawings described below are only some of the embodiments of the disclosure, and other accompanying drawings can be obtained based on them without creative work for those of ordinary skill in the art.

FIG. 1 is a schematic diagram of an evolutionary tree of some of the characterized pAgos according to an embodiment of the disclosure.

FIG. 2 is a schematic diagram of sequence comparison of seventeen-sixteen characterized Ago proteins according to an embodiment of the disclosure.

FIG. 3 is a schematic diagram of KmAgo purity analyzed by the sodium dodecyl sulfate-polyacrylamide gel electrophoresis (SDS-PAGE) gel according to an embodiment of the disclosure.

FIG. 4 is a schematic diagram of the sequences including SEQ ID NO: 3. SEQ ID NO: 4. SEQ ID NO: 5, and SEQ ID NO: 6 of the target DNA, the target RNA, the ssDNA guide and the ssRNA guide for testing according to an embodiment of the disclosure.

FIG. 5 is a schematic diagram of detecting the KmAgo cleaving the target ssDNA according to an embodiment of the disclosure.

DETAILED DESCRIPTION OF EMBODIMENTS

Figure 6:
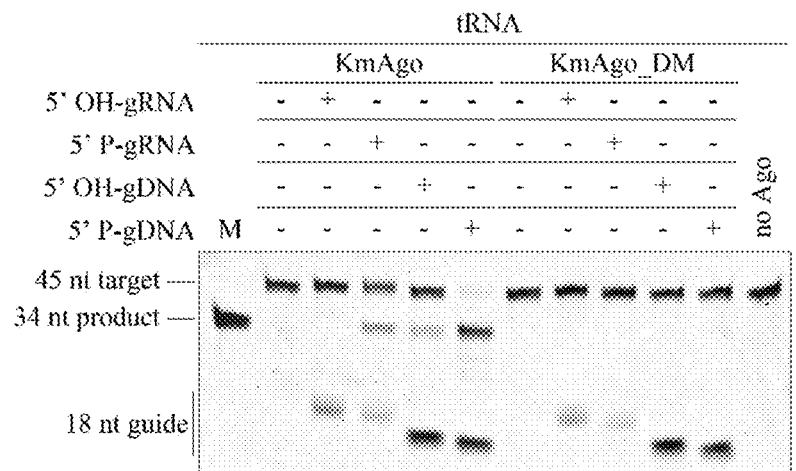
FIG. 6 is a schematic diagram of detecting the KmAgo cleaving the target RNA according to an embodiment of the disclosure.

In order to make the object, technical solutions and advantages of the disclosure more clearly understood, the disclosure is described in further detail hereinafter in connection with the embodiments. It should be understood that the specific embodiments described herein are intended to explain the disclosure only and are not intended to limit the disclosure.

In response to the problems of the prior art, the disclosure provides Argonaute proteins from prokaryotes and applications thereof, which are described in detail below in conjunction with the accompanying drawings.

The Argonaute protein from prokaryote (also referred to as prokaryotic Argonaute protein, shorted as pAgo) according to the embodiment of the disclosure is from the mesophilic prokaryote of *Kurthia massiliensis*, the prokaryotic Argonaute protein from the mesophilic prokaryote is named as KmAgo.

The Argonaute protein from prokaryote is the pAgo, the pAgo is consisted of an amino acid sequence as shown in SEQ ID NO: 1 or an amino acid sequence with at least 50% identity to the amino acid sequence as shown in SEQ ID NO: 1.

In an embodiment, the pAgo has at least 80%, preferably at least 90%, more preferably at least 95% sequence identity to the amino acid sequence as shown in SEQ ID NO: 1.

In an embodiment, the pAgo has a nuclease activity at 10 Celsius degrees (° C.) to 80° C., preferably at 32 to 44° C.

In an embodiment, the pAgo advantageously and preferably has the nuclease activity at 37° C.

An embodiment of the disclosure further provides a pAgo complex formed by the described above pAgo, a length of an ssDNA guide of the pAgo complex is 9 to 50 numbers of nucleotides, preferably 12 to 30 numbers of nucleotides, and more preferably 15 to 20 numbers of nucleotides, such as 16, 18 or 20 numbers of nucleotides.

In an embodiment, a length of an RNA guide of the pAgo complex is 10 to 30 numbers of nucleotides, preferably 12 to 25 numbers of nucleotides, and more preferably 12 to 18 numbers of nucleotides, such as 13, 15 or 18 numbers of nucleotides.

In an embodiment, target RNAs of the pAgo and of the pAgo complex respectively are no highly-structured; or, are highly-structured.

In an embodiment, target RNAs of the respective pAgo and pAgo complex each are no highly-structured, or are highly-structured.

In an embodiment, the target RNAs of the respective pAgo and pAgo complex each are the dsRNA.

In an embodiment, the target RNAs of the respective pAgo and pAgo complex each are an in vitro transcribed RNA.

In an embodiment, the target RNAs of the respective pAgo and pAgo complex each are a viral genomic RNA.

In an embodiment, the target RNAs of the respective pAgo and pAgo complex each are one of a messenger RNAs (i.e., mRNA) and other intracellular RNAs.

In an embodiment, guides of the respective pAgo and pAgo complex each are a 5'-terminal phosphorylated ssDNA.

In an embodiment, the guides of the respective pAgo and pAgo complex each are a 5'-terminal hydroxylated ssDNA.

In an embodiment, the guides of the respective pAgo and pAgo complex each are a 5'-terminal phosphorylated RNA.

In an embodiment, nuclease activities of the respective pAgo and pAgo complex requires the presence of at least one cation selected from the group consisting of manganese ion ($Mn^{2+}$), magnesium ion ($Mg^{2+}$), calcium ion ($Ca^{2+}$), copper ion ($Cu^{2+}$), iron ion ($Fe^{2+}$), cobalt ion ($Co^{2+}$), zinc ion ($Zn^{2+}$) and nickel ion ($Ni^{2+}$) and any combinations thereof.

In an embodiment, at least one cation of the respective pAgo and pAgo complex is $Mn^{2+}$.

In an embodiment, the pAgo and a pAgo of the pAgo complex both are extracted or synthesized.

In an embodiment, a target DNA of the pAgo is the ssDNA.

In an embodiment, the target DNA of the pAgo is the dsDNA.

An embodiment of the disclosure further provides a polynucleotide encoding the described above pAgo.

An embodiment of the disclosure further provides a method of in vitro cleaving RNA based on the pAgo; the method of in vitro cleaving RNA based on the pAgo includes:

step 1, forming a pAgo-guide complex based on the pAgo and an ssDNA guide;

step 2, making the pAgo-guide complex be in contact with a target RNA, the target RNA has a nucleotide sequence complementary to more than half of a sequence of the ssDNA guide, and the pAgo-guide complex cleaves the target RNA at a specific site.

Another object of the disclosure is to provide a method of intracellular cleaving target RNA based on the pAgo; the method of intracellular cleaving target RNA includes:

(1) mixing the pAgo with an ssDNA guide to form a pAgo-guide complex according to the pAgo with the ssDNA guide;

(2) transferring the pAgo-guide complex into a cell by transformation, transfection or transduction; a sequence of the ssDNA guide is complementary paired with more than half of a sequence of an RNA in the cell.

In an embodiment, the method of intracellular cleaving target RNA occurs in a cell in situ of a living tissue, an organ, or an animal including a human.

An embodiment of the disclosure further provides a method for the site-specifically modifying genetic material of cell based on the pAgo, the method for the site-specifically modifying genetic material of cell includes:

Introducing an expression vector containing a polynucleotide sequence of the pAgo into a cell, introducing one or more ssDNA guides simultaneously or not simultaneously, and expressing the pAgo in the cell. It is worth mentioning here, the introducing one or more ssDNA guides simultaneously or not simultaneously means introducing the expression vector and the ssDNA guides into the cell at the same time or introducing the expression vector and the ssDNA guides into the cell at the different time.

In an embodiment, the method for the site-specifically modifying genetic material of cell occurs in an isolated cell.

In an embodiment, the method for the site-specifically modifying genetic material of cell occurs in a cell in situ of a living tissue, an organ or an animal including a human.

In an embodiment, the pAgos are encoded by one expression vector.

In an embodiment, the expression vector containing the polynucleotide sequence of the pAgo is contained in a viral vector.

In an embodiment, the cell is a prokaryotic cell.

In an embodiment, the cell is a eukaryotic cell.

An embodiment of the disclosure further provides a viral vector including the described above expression vector.

The viral vector is a lentiviral vector or a retroviral vector.

An embodiment of the disclosure further provides a kit including the described above pAgo and the ssDNA guide.

FIG. 1 is a schematic diagram of an evolutionary tree of some of the characterized pAgos according to the embodiment of the disclosure.

The technical effects of the disclosure are further described below in connection with specific embodiments.

Embodiment 1 KmAgo Expression and Purification

The pET28a-KmAgo plasmid was transferred to *Escherichia coli* BL21 (DE3), and single colonies were inoculated into Luria-Bertani (LB) liquid medium containing 50 μg/mL kanamycin and shaking cultured in a shaker at 37° C. and 220 Revolutions Per Minute (rpm). When the optical density 600 (OD600) of the bacteria reached 0.8, the bacteria were transferred to a shaker at 18° C. overnight. The bacteria were collected by centrifugation at 6000 rpm for 10 min and after washing with Buffer A (Tris(hydroxymethyl)methyl aminomethane THAM-hydrochloride (shorted as Tris-HCl) with 20 milli mol/L (mM) and pH 7.5, Sodium chloride (shorted as NaCl) with 500 mM, and imidazole with 10 mM), the bacteria were resuspended in Buffer A, and the final concentration of 1 mM Phenylmethylsulfonyl fluoride (shorted as PMSF) was added and crushed at high pressure. 18000 rpm centrifugation was performed for 30 min, and the supernatant was collected. The supernatant was filtered and purified by Ni-NTA.

Nine column volumes were washed (added in three times) by using respect 10 mM imidazole and 20 mM imidazole and three-column volumes were washed by using respect 50 mM, 80 mM, 100 mM, 150 mM, 200 mM, 250 mM, 300 mM, and 1 M, and samples were taken for dodecyl sulfate, sodium salt (SDS)-Polyacrylamide gel electrophoresis (PAGE) detection. The eluted fractions containing high purity target proteins were collected and ultrafiltered to Buffer B (20 mM 4-(2-hydroxyethyl)-1-piperazine ethanesulfonic acid (HEPES) pH 7.5, 500 mM NaCl, 1 mM Dithiothreitol (DTT)). After dilution of NaCl concentration to 125 mM with 20 mM HEPES and pH 7.5, performing heparin columns (such as HiTrap Heparin HP, GE Healthcare) purification. The heparin column was pre-equilibrated with Buffer C (20 mM HEPES and pH 7.5, 125 mM NaCl and 1 mM DTT) and KmAgo was eluted by increasing the concentration of NaCl. heparin-purified proteins were purified by molecular sieves (such as Superdex 200 16/600 column, GE Healthcare), which were pre-equilibrated with Buffer D (20 mM HEPES pH 7.5, 500 mM NaCl and 1 mM DTT). Purified proteins were collected and identified purity using SDS-polyacrylamide gels (see FIG. 3). The proteins were divided into small portions, snap-frozen in liquid nitrogen and stored at −80° C.

FIG. 2 shows the region where the catalytic DEDX tetramer is located and the sequence identity of KmAgo and other Ago. FIG. 3 shows the gel analysis KmAgo results after through the Ni-NTA column and the heparin column, and finally using molecular sieves to purify KmAgo. The expected size of KmAgo is 82 kilo Dalton (kDa), which is calculated by using http://www.expasy.org/.

Embodiment 2 Testing Cleavage Activity of KmAgo

In order to assess which combinations of RNA/DNA guides and RNA/DNA targets KmAgo is able to cleave, activity assays were performed for all possible combinations. The cleavage assays were all performed at 37° C. in a 4:2:1 (pAgo: guide: target) molar ratio. 800 nano mol/L (nM) KmAgo was mixed with 400 nM guide in a reaction buffer containing HEPES-Sodium hydroxide (NaOH) with 10 mM and pH 7.5, NaCl with 100 mM, Manganese(II) chloride ($MnCl_2$) with 5 mM and 5% glycerol and incubated at 37° C. for 10 min for guide loading. The nucleic acid target was added to 200 nM. After 1 h of reaction at 37° C., the reaction was terminated by mixing the sample with 2×RNA loading dye (95% formamide, 18 mM Edetic acid (EDTA) and 0.025% Sodium dodecyl sulfate (SDS) and 0.025% bromophenol blue) and heating at 95° C. for 5 min. The lysis products were resolved by 20% denaturing PAGE, stained with SYBR Gold (such as Invitrogen) and visualized with Gel Doc™ XR+ (Bio-Rad).

No product band (34 nt) was observed in the DNA/RNA (guide/target) control assay incubated in the absence of KmAgo, indicating that product band formation is a result of KmAgo nuclease activity. KmAgo can cleave target DNA and RNA by using both 5'-phosphorylated DNA guide and 5'-hydroxylated DNA guide, and also cleaves target DNA and target RNA using 5'-phosphorylated RNA (see FIG. 5 and FIG. 6).

The arrows in FIG. 4 indicate the predicted cleavage sites. FIG. 5 shows that KmAgo can cleave target ssDNA after combining ssDNA guide and RNA guide. FIG. 6 shows that KmAgo can cleave target RNA after combining ssDNA guide and RNA guide.

Embodiment 3 KmAgo can Cleave Target RNA at Very Low $Mn^{2+}$ Concentrations

The next activity assay focused on finding the range of $Mn^{2+}$ concentrations at which KmAgo exhibited guide-mediated target RNA cleavage within 15 min. The $Mn^{2+}$ concentration range was set to 0 to 10 mM, and target RNA was efficiently cleaved (see FIG. 7) when $Mn^{2+}$ concentration is 0.01 mM and the guide was 5'-phosphorylated DNA; and the target RNA was efficiently cleaved (see FIG. 8) when the $Mn^{2+}$ concentration is greater than 0.5 mM and the guide was 5'-phosphorylated RNA.

Figure 7:
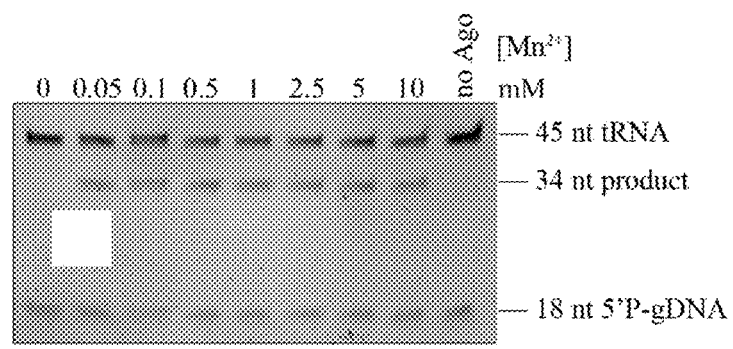
FIG. 7 is a schematic diagram of urea/polyacrylamide gel for determining target RNA/DNA guide products at different $Mn^{2+}$ concentrations according to an embodiment of the disclosure.

FIG. 7 shows that the DNA guide was incubated with KmAgo for 10 min at room temperature before adding the target, the 34 nt product band appears between 0.05-10 mM, and indicating the effective reaction.

Figure 8:
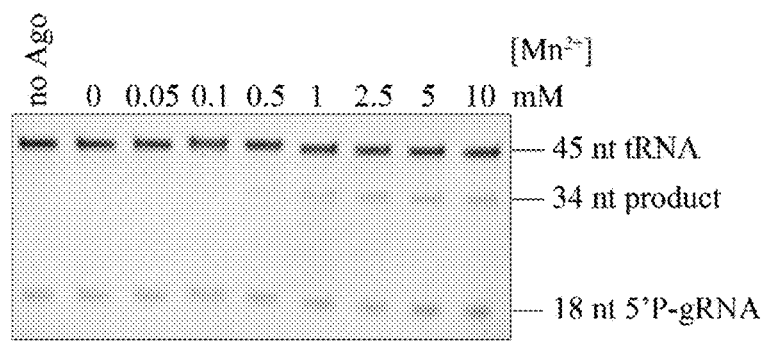
FIG. 8 is a schematic diagram of urea/polyacrylamide gel for determining target RNA/RNA guide products at different $Mn^{2+}$ concentrations according to an embodiment of the disclosure.

FIG. 8 shows that the RNA guide was incubated with KmAgo for 10 min at room temperature before adding the target, the 34 nt product band appears between 0.05-10 mM and indicates the effective reaction.

Embodiment 4 KmAgo can Cleave RNA at the Mesophilic Temperature

The next activity assay focused on finding the temperature range in which KmAgo exhibited guide-mediated target RNA cleavage within 15 min. The temperature range was set to 25 to 80° C., and when the guide is 5'-phosphorylated DNA, the target RNA can be cleaved at 25-75° C., of which 30-55° C. is the best (see FIG. 9); and when the guide was 5'-phosphorylated RNA, the target RNA can be cleaved at 25-50° C., of which 37-45° C. is the best (see FIG. 10).

Figure 9:
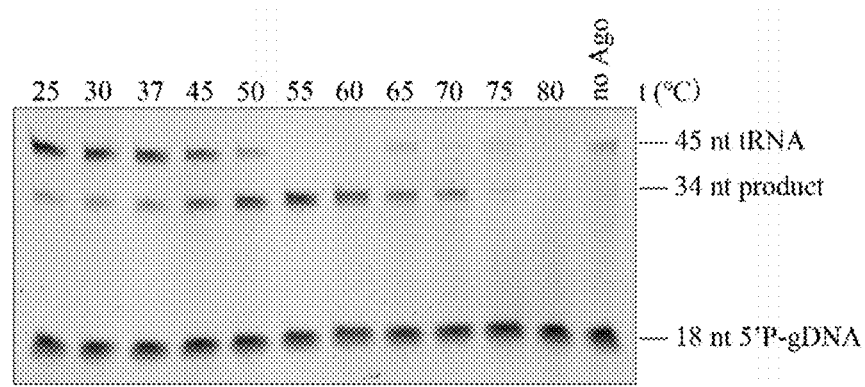
FIG. 9 is a schematic diagram of urea/polyacrylamide gel for determining target RNA/DNA guide products at different temperatures according to an embodiment of the disclosure.

FIG. 9 shows that the DNA guide was incubated with KmAgo for 10 min at room temperature before adding the target, the 34 nt product band appears between 25-75° C., and indicating the effective reaction.

Figure 10:
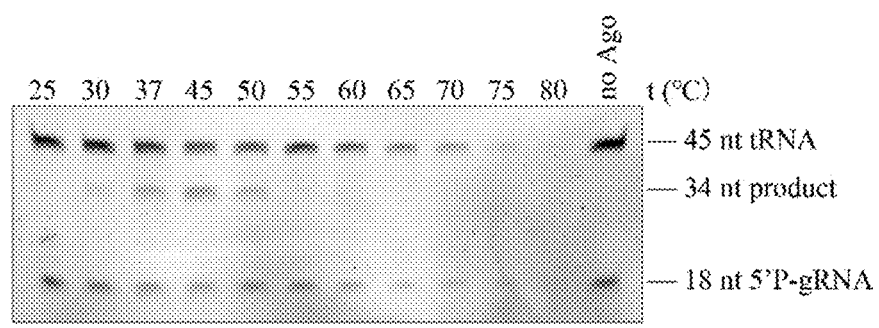
FIG. 10 is a schematic diagram of urea/polyacrylamide gel for determining target RNA/RNA guide products at different temperatures according to an embodiment of the disclosure.

FIG. 10 shows that the DNA guide was incubated with KmAgo for 10 min at room temperature before adding the target, the 34 nt product band appears between 25-50° C. and indicates the effective reaction.

Figure 11:
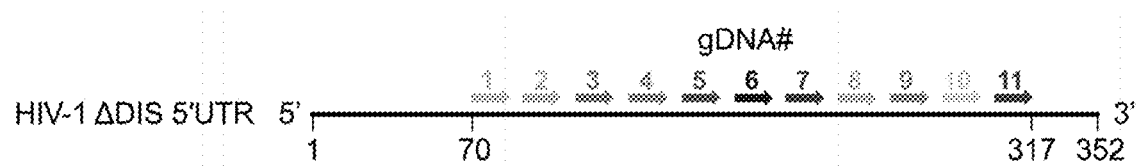
FIG. 11 is a schematic diagram of DNA guide design for targeting highly-structured RNA and the sequence of HIV-1 ΔDIS 5'UTR according to an embodiment of the disclosure.

Embodiment 5 KmAgo can Cleave Highly-Structured Target RNA at Mesophilic Temperature The prior art HIV-1 ΔDIS 5'UTR is a highly structured RNA (see FIG. 11). The HIV-1 ΔDIS 5'UTR was transcribed in vitro using T7 RNA polymerase and the synthetic DNA template with the T7 promoter sequence. Transcripts for the cleavage assay were treated with DNase I and gel purified. The disclosure was designed with 11 numbers of gDNAs (the length of the gDNA is 18 nt) to guide KmAgo cleaving at different sites. Cleaving products were detected at the expected positions at all sites, albeit to varying degrees (see FIG. 12), suggesting that the KmAgo-gDNA complex cleaves target RNA sequences even in highly structured RNAs.

FIG. 11 shows that the DNA guide was incubated with KmAgo for 10 min at room temperature before adding the target, the 34 nt product band appears between 25-50° C., and indicating the effective reaction.

Figure 12:
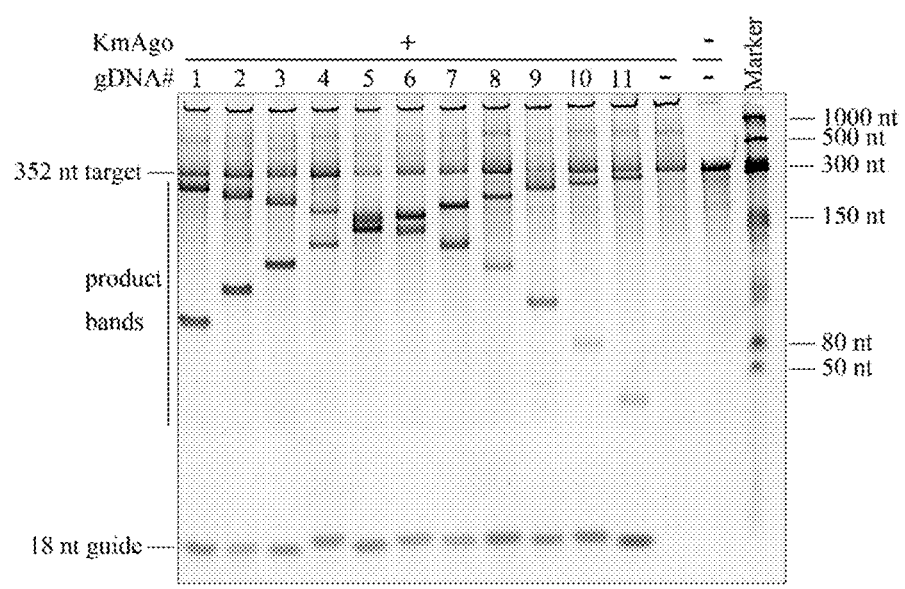
FIG. 12 is a schematic diagram of urea/polyacrylamide gel for testing highly-structured RNA cleavage products according to an embodiment of the disclosure.

FIG. 12 shows that the DNA guide was incubated with KmAgo for 10 minutes at room temperature before adding the target, predicted bands appearing for all reactions, and indicating the effective reaction.

Embodiment 6

The disclosure provides a pAgo from the mesophilic prokaryote of *kurthia massiliensis*, and named as KmAgo.

A first aspect of the disclosure relates to providing the pAgo including an amino acid sequence as shown in SEQ ID NO: 1 or an amino acid sequence with at least 50% identity to the amino acid sequence as shown in SEQ ID NO: 1, the pAgo has binding activity for the ssDNA guides or the RNA guides and has nuclease activity for target DNAs and/or target RNAs, such that site-specific cleavage of the target DNA and/or the RNA occurs when the ssDNA guide and/or the RNA guide that have the sequence paired with more than half of the sequence of the target RNA and/or the DNA bind to the pAgo to form the pAgo-guide complex and the pAgo-guide complex is conjugated to the target RNA and/or the DNA.

A second aspect of the disclosure relates to providing a pAgo including a polynucleotide sequence as shown in SEQ ID NO. 2 or a polynucleotide sequence preferably hybridizable to the polynucleotide sequence as shown in SEQ ID NO. 2 under stringent conditions, the pAgo of the second aspect has binding activity for ssDNA guides or RNA guides and has nuclease activity for target DNA and/or RNA, such that site-specific cleavage of the target RNA and/or the DNA occurs when the ssDNA guide and/or the RNA guide that have the sequence substantial complementarity with the sequence of the target RNA and/or the DNA bind to the pAgo to form the pAgo-guide complex and the pAgo-guide complex is conjugated to the target RNA and/or the DNA.

A third aspect of the disclosure relates to providing a method of in vitro cleaving RNA, which has the following steps: providing the pAgo as described herein and ssDNA guide and/or RNA guide, forming the pAgo-guide complex according to the guide and the pAgo; making the pAgo-guide complex be in contact with the target RNA, the target RNA having a nucleotide sequence that is mostly complementary with the sequence of the guide, the pAgo-guide complex cleaves the target RNA at a specific site.

Preferably, the length of the pAgo of the disclosure is 737 numbers of amino acids in, or may be a longer or shorter length of contiguous amino acids. the number of the amino acids (longer or shorter) can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, or 250.

Thus, the above contiguous amino acids are defined to include functional fragments that are less than the full length of the pAgo described in the disclosure (such as 737 amino acids), but retain site-specific cleavage activity of the target RNA and the pAgo-guide complex formed with the guide.

When using the pAgo in the first and second aspects of the disclosure, preferably they are identical, but need not necessarily be so.

The ssDNA guide and/or RNA guide is substantially complementary to the target RNA, meaning that the guide is either fully complementary to the same length of sequence contained in the target RNA or there are many mismatches (usually segregated or possibly contiguous). The number of mismatches may be 1, 2, 3, 4 or 5, etc.

The pAgo may have at least 80%, preferably at least 90%, more preferably at least 95% sequence identity with the amino acid sequence as shown in SEQ ID NO: 1.

Optionally, the pAgo of the disclosure contains a nuclear localization sequence (NLS) at either the 5'-terminal or the 3'-terminal or both terminals. It is contemplated that the pAgo of the disclosure has multiple NLSs at the 5'-terminal or 3'-terminal or both terminals.

In a preferred embodiment, the pAgo has nuclease activity in the temperature range of 10 to 80° C., preferably 32 to 44° C., more preferably, at 37° C.

Preferably, the length of the ssDNA guide forming the pAgo complex is 9-50 numbers of nucleotides, preferably 12-30 numbers of nucleotides, and more preferably 15-20 numbers of nucleotides, such as 16, 18 or 20 numbers of nucleotides.

Preferably, the RNA guide forming the pAgo complex has a length of 10-30 numbers of nucleotides, preferably 12-25 numbers of nucleotides, and more preferably 12-18 numbers of nucleotides, such as 13, 15, or 18 numbers of nucleotides.

In some embodiments, the target RNA is no highly-structured. In other embodiments, the target RNA is highly-structured. Other possible target RNA includes double-stranded RNA, in vitro transcribed RNA, viral genomic RNA, messenger RNA (mRNA), and other intracellular RNAs.

The guide may be 5'-terminal phosphorylated ssDNA and/or RNA or hydroxylated ssDNA. the guide may contain a terminal 5'-triphosphate.

Preferably, the nuclease activity of the pAgo of the disclosure requires the presence of at least one cation selected from the group consisting of $Mn^{2+}$, $Mg^{2+}$, $Ca^{2+}$, $Cu^{2+}$, $Fe^{2+}$, $Co^{2+}$, $Zn^{2+}$ and $Ni^{2+}$ and any combinations thereof. A particularly preferred the cation is $Mn^{2+}$. The concentration range of the cation used can vary from about 0.01 mM to about 2000 mM. Particularly preferably, the range is from about 0.05 mM to about 20 mM.

A fourth aspect of the disclosure provides a method of intracellular cleaving target RNA, including the steps of.
1) mixing the pAgo as defined herein with the ssDNA guide and/or the RNA guide;
2) forming a pAgo-guide complex according to the pAgo and the guide;
3) transferring the pAgo-guide complex into a cell by transformation, transfection or transduction;
4) Preferably, the sequence of the guide is complementarily paired with more than half of the sequence of a RNA in the cell.

A fifth aspect of the disclosure provides a method for the site-specifically modifying genetic material of cell by introducing an expression vector containing the polynucleotide sequence of the pAgo described herein into the cell, and introducing one or more ssDNA guides simultaneously or not simultaneously, thereby expressing the pAgo described herein within the cell.

In some embodiments, the method for the site-specifically modifying genetic material of cell occurs in the isolated cell. In other embodiments, the method for the site-specifically modifying genetic material of cell may occur in the cell in situ of the living tissue, the organ, or the animal including the human. The pAgo of the method may be encoded by one expression vector. In other such methods, one or more the pAgo may be encoded by two expression vectors. In some embodiments, the methods of the disclosure may include an expression vector encoding all pAgos. This expression vector in some methods of the disclosure may be contained in a viral vector, such as a lentiviral vector or a retroviral vector.

The method for the site-specifically modifying genetic material of cell described in the disclosure may be used in the prokaryotic cell. In other embodiments, the method for the site-specifically modifying genetic material of cell described herein may be used in the eukaryotic cell.

A sixth aspect of the disclosure provides a kit. Kit 1 contains the pAgo as described herein, and at least one ssDNA guide and/or RNA guide. Kit 2 contains the expression vector as described herein, and ssDNA guide and/or RNA guide. Optionally, kit 3 contains a viral vector as described herein and a viral vector encoding an ssDNA guide and/or RNA guide.

A seventh aspect of the disclosure relates to providing a pAgo including an amino acid sequence as shown in SEQ ID NO: 1 or an amino acid sequence with at least 50% identity to the amino acid sequence as shown in SEQ ID NO: 1, which has binding activity for the ssDNA guide or RNA guide, and has no nuclease activity for target DNA and target RNA, such that site-specific blockage of target RNA or target DNA occurs when the ssDNA guide and/or the RNA guide that have the sequence paired with more than half of the sequence of the target RNA and/or the target DNA bind to the pAgo to form the pAgo-guide complex and the pAgo-guide complex is conjugated to the target RNA.

The absence of nuclease activity, particularly nucleic acid endonuclease activity, is caused by mutating one or more amino acid residues essential for the catalytic activity of the pAgo. That is, mutating at least one amino acid located in the evolutionarily conserved amino acid tetrad (DEDD/H). Thus, the mutation could be a single amino acid change in any one or more of the following amino acid sequence portions of the pAgo:

FIGIDVSHE
ILAGEKIDD
TIHRDGFWR
IHYADLSAT.

More particularly, the amino acid change is a single change at one or more of the above-highlighted residues. Preferably, the single mutation is a non-conservative substitution, for example from D to A, or from E to A. Thus, any substitution other than D to E or E to D is possible.

In addition to the substitution, one or more highlighted residues may be simply deleted, optionally, one or more amino acids within the sequence motif may be deleted consecutively or discontinuously. One or more sequence motifs may be deleted in their entirety. Any combination of the above changes can be made, such as one motif non-conservative change and the other three motifs missing.

The structural features of the nuclease-deficient pAgo of the disclosure may also include any of the structural changes as defined above with respect to having nuclease-active pAgos. For example, the range of sequence identity compared to the reference sequence, the composition of the pAgo with respect to the amino acid structural domain, and the total length with respect to the amino acid. The definition of the guide is similar to the guide that was used for the pAgos with nuclease active in the disclosure.

In a seventh aspect of the disclosure, the pAgo-guide complex has no nuclease active, which means that advantageously there exists a method for blocking specific sites in target DNA or RNA by specific sequence recognition, and the targets can be single-stranded and double-stranded. Such site-specific blocking provides a precise means of blocking transcription of the target gene, or blocking, disrupting or interfering with specific sites involved in the regulation of gene expression.

Accordingly, the disclosure further provides an in vitro method for site-specific targeted blockade of target DNA or target RNA including the steps of: providing the pAgo without nuclease activity as described herein and ssDNA guide and/or RNA guide, forming a pAgo-guide complex according to the guide and the pAgo; making the pAgo-guide complex be in contact with the target RNA or the target DNA, the target having a nucleotide sequence that is substantially complementary to the sequence of the guide, and the pAgo-guide complex binds to a region on the target that is substantially complementary to the guide.

Alternatively, the disclosure provides a method for site-specific blocking of a targeting polynucleotide in the cell, including the steps: mixing the pAgo without nuclease activity as defined herein and ssDNA guide to form a pAgo-guide complex according to the pAgo and the guide; transferring the pAgo-guide complex into a cell, such as by transformation, transfection or microinjection, and the guide sequence and a segment of DNA or RNA sequence contained in the target DNA or RNA are substantially complementary.

In addition, the disclosure provides a method for site-specific targeting blockade of target DNA or target RNA in cell, the method includes the steps of:
1) transfecting, transforming or transducing the cells with the expression vector encoding the pAgo without nuclease activity as described above;
2) transfecting, transforming or transducing a first ssRNA guide sequence and a second ssRNA guide sequence;
3) at least one of the sequences of the guide is substantially complementary to a DNA or RNA sequence contained in the target DNA or target RNA, and expressing the pAgo-guide complex in the cell, the pAgo-guide complex is formed by the pAgo and the RNA guide and can block the specific site.

Advantageously, the method for site-specific blockade of target polynucleotides using the pAgos without nuclease activity of the disclosure can be targeted to disrupt gene expression, and/or control elements of gene expression, such as promoters or enhancers. Among the various methods for site-specific blocking of target DNA or target RNA, particularly preferred or optional aspects refer to the nuclease activity pAgos defined in the disclosure.

Embodiment 7

SEQ ID NO:1 as shown below is the amino acid sequence of the KmAgo.

Met Glu Ala Tyr Ile Thr Glu Met Val Ser Arg Glu Arg

Ala Asn Glu Leu Glu Val Tyr Val Tyr Val Phe Pro Arg

Lys Gln Ser Asp Asn Asn Tyr Glu Gly Val Tyr His Ile

Met Arg Ala Trp Gln Arg Ala Asn Asp Leu Pro Leu Ala

Tyr Asn Gln His Thr Ile Met Ala Phe Ser Pro Val Arg

His Met Cys Gly Tyr Thr Pro Met Glu Thr Gln Lys Arg

His Ile Asn Ile Asp Ser Pro Phe Glu Arg Ala Leu Leu

Glu Arg Leu Ile Lys Asn Ser Leu Ile Phe Thr Ala Glu

Arg His Leu His Ala Lys Arg Val Gly His Ala Leu Arg

Leu Asn Gln Val Gln Gln Ile Arg Gln Val Ile Ile Tyr

Glu Ala Ile Glu Leu Tyr Val Asn Ile Ile Glu Asn Arg

Ile Ser Ile Gly Phe His Leu Thr His Gln Phe Glu Tyr

Val Tyr Thr Leu Gln Ser Met Ile Glu Gln Gly Lys Thr

Ile Arg Pro Gly Met Arg Val Val His Ser Asn Gly Arg

Gln His Tyr Thr Tyr Thr Val Glu Asn Val Ala Thr Tyr

Gly Val Thr Asp Arg Cys Pro Leu Leu Gln Thr Ser Ile

Tyr Gln Tyr Tyr Val Glu Lys Gly Ala Gln His Ile Leu

Arg Thr Phe Thr Arg Ser Thr Arg Val Ile His Val Arg

Thr Lys Glu Gln Arg Leu Ser Tyr Ala Ala Thr Leu Leu

Lys Pro Leu Cys Thr Phe Glu Thr Met Gln Pro Gln Asp

Val Leu Asn Val Ser Lys Cys Ile Lys Leu Ser Ala Ser

Lys Arg Met Lys Cys Thr Tyr Arg Trp Ile Gln Gln Leu
Arg Ala Gln Tyr Arg His Leu Thr Phe Ala Pro Asn Pro
Phe Thr Ile Ala Gln Asn Gly Tyr Lys Leu Asp Gln Leu
Ser Thr Pro Lys Val His Phe His Arg Asp Tyr Ala Thr
Val Val Ser Gly Met Lys Thr Gly Lys Leu Tyr Lys Gly
Gly Asn Ile Lys Ile Ser Val Leu Phe Asp Glu Asp Phe
Tyr Leu Lys His His Ile Thr Lys Lys Asp Ile Tyr Gln
Phe Ile Ala Val Leu Gln Lys Ile Ala Ile Ala Gln Gly
Val Asn Met Thr Ile Ser Thr Ser Thr Lys Ser Ile Thr
Gly Lys Phe Thr Asp Asp Phe Phe His His Phe Thr Glu
Glu Val Glu Ala Leu Gln Pro Ile Phe Ala Gln Thr Thr
Val Leu Ala Phe Ile Thr Ser Thr His Leu Ser Asn Lys
Lys Thr Arg Ser Tyr Gln Leu Leu Lys Gln Tyr Phe Gly
Gly Lys Trp Asp Ile Ala Ser Gln Val Ile Thr Glu Lys
Thr Ile Glu Ala Phe Gln Lys Ile Leu His Lys His Gly
Leu Lys Asn Phe Tyr Pro Asn Asp Glu Gln His Cys Leu
Arg Val Ile Asp Val Leu Lys Asn Glu Ser Phe Tyr Tyr
Thr Val Met Asn Ile Leu Leu Gly Val Tyr Val Lys Ser
Gly Ile Gln Pro Trp Ile Leu Ala Asn Thr Thr His Ser
Asp Cys Phe Ile Gly Ile Asp Val Ser His Glu Asn Gly
Asn Ser Ala Ala Gly Met Met Asn Val Ile Gly Ser Gln
Gly His Leu Ile Gln Gln Ala Pro Leu Asn Gly Ile Leu
Ala Gly Glu Lys Ile Asp Asp Thr Leu Leu Ala Asn Leu
Leu Lys Gln Met Ile Lys Ala Tyr His Thr Gln Phe Gln
Arg Phe Pro Lys His Ile Thr Ile His Arg Asp Gly Phe
Trp Arg Glu His Thr Ala Leu Val Glu Lys Lys Pro Asn
Arg Arg Met Ala Phe Phe Asn Ser Val Asp Asn Thr Phe
Ser Thr Arg Gln Gly Thr Val Tyr Gln Arg Gly Asn Glu
Ala Phe Leu Cys Ala Thr Asn Pro Gln Gln Lys Val Gly
Met Ala Gln Pro Ile Lys Ile His Gln Val Thr Lys Thr
Leu Pro Phe Ser His Ile Ile Glu Asp Val Tyr Asn Leu
Ser Phe Leu His Ile His Ala Met Asn Lys Met Arg Leu
Pro Ala Thr Ile His Tyr Ala Asp Leu Ser Ala Thr Ala
Tyr Gln Arg Gly Gln Val Met Pro Arg Ser Gly Asn Gln
Thr Asn Leu Pro Phe Val

SEQ ID NO:2 as shown below is the polynucleotide sequence of the KmAgo.

atggaagcttacatcaccgagatggtgtccagagaaagagctaacgagttg
gaggtttacgtctacgtgttcccaagaaagcagtccgacaacaactacgag
ggtgtctaccacattatgagagcttggcaaagagccaacgacttgccattg
gcttacaaccagcacaccatcatggctttctcaccagttagacacatgtgc
ggttacaccccaatggaaactcagaagagacacatcaacatcgactcccca
ttcgagagagctttgttggagagactgatcaagaactccttgatcttcact
gccgagagacacttgcatgctaagagagttggtcacgccttgagattgaac
caggttcagcaaatcaggcaggtcatcatctacgaggctatcgagttgtac
gtcaacatcatcgagaacaggatctccatcggtttccacttgactcaccaa
ttcgagtacgtctacaccctgcagtccatgattgagcagggtaagactatc
agaccaggtatgagagttgtccactccaacggtagacagcactacacttac
accgttgagaacgttgctacctacggtgttactgacagatgtcctttgttg
cagacctccatctaccagtactacgttgagaagggtgctcagcacatcttg
agaactttcaccagatccaccagagtcatccacgttaggaccaaagagcag
agattgtcctacgctgctaccttgttgaagccattgtgtaccttcgagact
atgcagccacaggacgttttgaacgtttccaagtgcatcaagttgtccgcc
tccaagagaatgaagtgcacctacagatggattcagcagttgagagcccag
tacagacacttgactttcgccccaaatccattcactatcgcccagaacggt
tacaagttggaccagttgtctaccccaaaggtccacttccatagagactac
gctactgttgtctccggtatgaagaccggtaagttgtacaaaggtggtaac
atcaagatctccgtcctgttcgatgaggacttctacttgaagcaccacatc
accaagaaggatatctaccaattcattgccgtcctgcagaagatcgctatt
gctcagggtgttaacatgaccatctccacctccactaagtccatcactggt
aagttcaccgacgatttcttccaccacttcaccgaagaggttgaagccttg
caacctatcttcgctcagactactgttctggccttcatcacttctacccac
ctgtccaacaagaaaaccaggtcctaccaattgctgaagcagtactttggt
ggtaagtgggacattgcttcccaggttatcaccgaaaagactatcgaggcc
ttccaaaagatcctgcacaagcacggtctgaagaacttttacccaaacgac
gagcagcactgcttgagagttattgacgtcttgaagaacgagtccttctac
tacaccgtcatgaacatcctgctgggtgtttacgttaagtccggtattcag
ccatggatcttggctaacactactcactccgactgcttcatcggtattgac
gtttctcacgagaacggtaactctgctgctggtatgatgaacgttattggt
tcccagggtcacttgatccaacaggctccattgaacggtattttggccggt
gaaaagatcgacgacaccttgttggccaatctgttgaagcagatgatcaag
gcctaccacactcagttccagagattcccaaagcacatcactatccaccgt
gacggttttggagagaacacactgctttggtcgagaagatcatgtctcac
tacgagatcaccctacgacatcgtcgagatcatcaaaaagccaaacagaagg
atggccttcttcaactccgttgacaacacttttctccaccagacagggtact
gtttaccagagaggtaacgaggctttcctgtgtgctacaaacccacagcaa
aaggttggtatggctcagccaatcaagattcaccaggttaccaagaccttg
ccattctctcacattatcgaggacgtgtacaacctgtccttcttgcacatt -continued

```
cacgccatgaacaagatgagattgccagccactattcactacgctgacttg tctgctactgcttaccaacgtggtcaggttatgcctagatctggtaaccag accaacctgccattcgtttaa
```

The above description is only exemplary embodiments of the disclosure, but the protection scope of the disclosure is not limited to this. Within the technical scope disclosed by the disclosure, any modification, equivalent replacement and improvement made within the spirit and principle of the disclosure by those skilled persons in the art shall be included in the protection scope of the disclosure.

What is claimed is:

1. A method of in vitro cleaving RNA based on an Argonaute protein from prokaryote (pAgo), comprising: forming a pAgo-guide complex based on the pAgo and a single-stranded deoxyribonucleic acid (ssDNA) guide; and making the pAgo-guide complex be in contact with a target RNA, wherein the target RNA has a nucleotide sequence complementary to more than half of a sequence of the ssDNA guide; and cleaving the target RNA by the pAgo-guide complex in the presence of manganese ions (Mn2+) and a temperature of 37° C.; and wherein the pAgo is from a mesophilic prokaryote of *Kurthia massiliensis*, and consisted consisting of the amino acid sequence as shown in SEQ ID NO:1.

2. The method as claimed in claim 1, wherein the concentration of the $Mn^{2+}$ is 0.01 millimoles per liter (mM).

3. The method as claimed in claim 1, wherein the sequence of the ssDNA guide is SEQ ID NO: 3, and the sequence of the target RNA is SEQ ID NO: 6.

4. The method as claimed in claim 1, wherein the cleaving the target RNA by the pAgo-guide complex in the presence of $Mn^{2+}$ and a temperature of 37° C. comprises: cleaving the target RNA by the pAgo-guide complex at the concentration of $Mn^{2+}$ and the temperature of 37° C. in a molar ratio of the pAgo:the ssDNA guide:the target RNA of 4:2:1.

5. A method of in vitro cleaving RNA based on pAgo, comprising:
  mixing 800 nanomoles per liter (nM) of the pAgo with 400 nM of ssDNA guide in a reaction buffer containing 10 mM of HEPES-sodium hydroxide (NaOH), 100 mM of sodium chloride (NaCl), 5 mM of manganese (II) chloride ($MnCl_2$) and 5% glycerol, and incubating at 37° C. for 10 min for guide loading, so as to obtain a pAgo-guide complex;
  adding 200 nM of target RNA into the pAgo-guide complex; and
  cleaving the target RNA by the pAgo-guide complex a molar ratio of the pAgo:the ssDNA guide:the target RNA of 4:2:1;
  wherein the pAgo is from a mesophilic prokaryote of *Kurthia massiliensis* with the amino acid sequence as shown in SEQ ID NO:1.

6. The method as claimed in claim 5, wherein the sequence of the ssDNA guide is SEQ ID NO: 3, and the sequence of the target RNA is SEQ ID NO: 6.

* * * * *